(12) United States Patent
Johnson

(10) Patent No.: US 9,907,324 B2
(45) Date of Patent: Mar. 6, 2018

(54) EFFERVESCENT COMPOSITION FOR FORMING A GELLED COMPOSITION, TABLET FOR FORMING A GELLED COMPOSITION, AND METHOD OF MAKING A GELLED COMPOSITION

(75) Inventor: Kyle M. Johnson, Plymouth, MN (US)

(73) Assignee: Amerilab Technologies, Inc., Plymouth, MN (US)

( * ) Notice: Subject to any disclaimer, the term of this patent is extended or adjusted under 35 U.S.C. 154(b) by 903 days.

(21) Appl. No.: 13/113,174

(22) Filed: May 23, 2011

(65) Prior Publication Data
US 2011/0287114 A1 Nov. 24, 2011

Related U.S. Application Data

(60) Provisional application No. 61/347,755, filed on May 24, 2010.

(51) Int. Cl.
| | | |
|---|---|---|
| A61K 31/167 | (2006.01) | |
| A61K 47/42 | (2017.01) | |
| A61K 33/06 | (2006.01) | |
| A23L 1/01 | (2006.01) | |
| A61P 25/04 | (2006.01) | |
| A23L 1/0562 | (2006.01) | |
| A61K 9/46 | (2006.01) | |
| A61K 9/00 | (2006.01) | |
| A61K 9/06 | (2006.01) | |
| A61K 9/20 | (2006.01) | |
| A61K 31/192 | (2006.01) | |
| B01J 13/00 | (2006.01) | |
| A61J 1/03 | (2006.01) | |
| A23P 10/28 | (2016.01) | |
| A23L 5/10 | (2016.01) | |
| A23L 29/281 | (2016.01) | |
| A23L 9/10 | (2016.01) | |

(52) U.S. Cl.
CPC ............ *A23L 1/05625* (2013.01); *A23L 5/15* (2016.08); *A23L 9/10* (2016.08); *A23L 29/284* (2016.08); *A23P 10/28* (2016.08); *A61J 1/03* (2013.01); *A61K 9/0007* (2013.01); *A61K 9/0056* (2013.01); *A61K 9/06* (2013.01); *A61K 9/2063* (2013.01); *A61K 31/167* (2013.01); *A61K 31/192* (2013.01); *A61K 47/42* (2013.01); *B01J 13/0052* (2013.01)

(58) Field of Classification Search
None
See application file for complete search history.

(56) References Cited

U.S. PATENT DOCUMENTS

| | | |
|---|---|---|
| 1,896,049 A | 1/1933 | Zeigler |
| 1,929,732 A | 10/1933 | Zeigler |
| 2,163,164 A | 6/1939 | Wickenden et al. |
| 3,137,630 A | 6/1964 | Hecker et al. |
| 3,445,242 A | 5/1969 | Schaafsma |
| 3,943,265 A | 3/1976 | Steensen et al. |
| 4,105,579 A | 8/1978 | Bateman |
| 4,224,353 A | 9/1980 | Kueper et al. |
| 4,500,552 A | 2/1985 | Kadison et al. |
| 4,574,091 A | 3/1986 | Steensen et al. |
| 4,749,684 A * | 6/1988 | Silvestrini .................... 514/20.7 |
| 4,895,889 A | 1/1990 | Kirk et al. |
| 5,587,180 A * | 12/1996 | Allen et al. ................... 424/499 |
| 5,665,782 A | 9/1997 | Alexander et al. |
| 5,760,094 A | 6/1998 | Alexander et al. |
| 6,020,003 A | 2/2000 | Stroh et al. |
| 6,403,140 B1 | 6/2002 | Tiainen et al. |
| 6,569,454 B2 | 5/2003 | Nguyen |
| 2002/0142992 A1 | 10/2002 | Scherr |
| 2003/0170301 A1 | 9/2003 | Wehling |
| 2005/0008677 A1 | 1/2005 | Modliszewski et al. |
| 2005/0158381 A1 | 7/2005 | Aldritt et al. |
| 2007/0275118 A1 | 11/2007 | Van Laere et al. |
| 2009/0269328 A1 | 10/2009 | Ishii et al. |

FOREIGN PATENT DOCUMENTS

| | | |
|---|---|---|
| EP | 1273239 A1 * | 1/2003 |
| EP | 1407677 A2 * | 4/2004 |
| GB | 466235 | 5/1937 |
| JP | 2001-172203 | 6/2001 |
| WO | WO 96/33694 | 10/1996 |
| WO | WO 99/59542 | 11/1999 |
| WO | WO 2008075333 A2 * | 6/2008 |

* cited by examiner

*Primary Examiner* — John Pak
*Assistant Examiner* — Daniel L Branson
(74) *Attorney, Agent, or Firm* — Allison Johnson, P.A.

(57) ABSTRACT

A method of making a gelled composition that includes combining water and an effervescent tablet in a vessel, the effervescent tablet including at least 200 mg gelatin and an effervescent couple that includes an acid and a base, heating an aqueous composition (e.g., in a microwave oven), optionally adding cold water to the heated composition, and chilling the composition for a period sufficient for the composition to form a gel.

40 Claims, No Drawings

EFFERVESCENT COMPOSITION FOR FORMING A GELLED COMPOSITION, TABLET FOR FORMING A GELLED COMPOSITION, AND METHOD OF MAKING A GELLED COMPOSITION

CROSS REFERENCE TO RELATED APPLICATIONS

This application claims priority to U.S. Provisional Application Ser. No. 61/347,755 filed May 24, 2010, and incorporated herein.

BACKGROUND

The invention is directed to forming a gel.

Gelatin dessert products often include a powder that includes gelatin, sugar, and a food grade acid. The acid has been described as useful for adjusting the pH of the gel and imparting tartness to the taste of the dessert.

Gelatin dessert products are often prepared by boiling water on a stove, placing the boiling water in a container such as a bowl, adding the gelatin powder to the boiling water, stirring, adding ice or cold water to the mixture and stirring, and then placing the liquid in a refrigerator. The acts of boiling water on a stove and transferring boiling water from a pot to a bowl can be very dangerous, especially for young children.

Effervescent tablets used for preparing beverages are most often tableted to a size of less than about 1 inch and less than about 6 grams. It is very difficult to include large amounts of active components in such tablets because there must be sufficient "room" in the tablet for the components that actually make the effervescent tablet both a tablet and effervescent, i.e., binders, lubricants, and the effervescent couple.

SUMMARY

In one aspect, the invention features a method of making a gelled composition, the method including combining a tablet that includes at least 200 mg gelatin and water in a vessel to form an aqueous composition, heating the aqueous composition in a microwave oven, the tablet at least partially dissolving during the heating, and chilling the aqueous composition for a period sufficient for the aqueous composition to form a gel. In one embodiment, the chilling occurs in an environment having a temperature of no greater than 8° C. In some embodiments, the composition forms a set gel in less than two hours when chilled at a temperature of from about 0° C. to about 8° C. In other embodiments, the tablet is an effervescent tablet that includes an effervescent couple that includes an acid and a base.

In other embodiments, the method further includes adding cold water having a temperature of from about 0° C. to about 25° C. to the heated aqueous composition.

In some embodiments, the gel is a set gel.

In one embodiment, combining the water and the tablet includes placing from about 1 ounce to about 3 ounces of water in the vessel.

In other embodiments, adding cold water includes adding from about 1 ounce to about 3 ounces of cold water.

In another embodiment, the tablet includes at least about 400 mg gelatin.

In some embodiments, combining the water and the tablet includes placing about 0.5 ounces of water in the vessel. In other embodiments, the method further includes adding about 0.5 ounces of cold water having a temperature of from about 0° C. to about 25° C. to the heated aqueous composition.

In another embodiment, the tablet includes at least about 1000 mg gelatin. In other embodiments, the tablet includes at least about 1500 mg gelatin. In some embodiments, the tablet includes from about 1000 mg to about 5000 mg gelatin.

In one embodiment, the composition forms a set gel in no greater than two hours.

In another aspect, the invention features a method of making a gelled composition, the method including heating an aqueous composition that includes an effervescent tablet and water, the effervescent tablet includes gelatin and an effervescent couple that includes an acid and a base, the tablet at least partially dissolving during the heating, and chilling the composition to form a set gel. In one embodiment, heating includes heating the aqueous composition in a microwave oven. In some embodiments, the effervescent tablet includes at least 1000 mg of the gelatin. In one embodiment, the method further includes adding cold water having a temperature of no greater than 25° C. to the heated water. In some embodiments, adding cold water includes adding from about 1 ounce to about 3 ounces of cold water, the cold water having a temperature of from about 0° C. to about 25° C.

In another embodiment, the method includes placing an effervescent tablet that includes gelatin and an effervescent couple that includes an acid and a base in a vessel, placing from about 1 ounces to about 3 ounces of tap water in the vessel to form an aqueous composition, heating the aqueous composition, the tablet at least partially dissolving during the heating, adding from about 1 ounce to about 3 ounces of cold water having a temperature of no greater than 25° C. to the heated aqueous composition, and chilling the heated aqueous composition to form a set gel, the chilling including placing the aqueous composition in a refrigerator.

In other aspects, the invention features an effervescent composition that includes from about 10% by weight to about 30% by weight of an effervescent couple that includes an acid and a base, from at least 5% by weight to about 20% by weight of the acid, from at least 1% by weight to about 15% by weight of the base, and at least 200 mg gelatin. In some embodiments, the effervescent composition includes from about 10% by weight to about 20% by weight of the acid and from at least 5% by weight to about 15% by weight of the base.

In one embodiment, the effervescent composition is an effervescent tablet that includes at least 30% by weight of the gelatin, and further includes from about 5% by weight to about 40% by weight binder, and from about 0.5% by weight to about 1% by weight lubricant. In another embodiment, the tablet includes at least about 1000 mg gelatin. In other embodiments, the tablet includes at least about 1500 mg gelatin. In one embodiment, the tablet has a hardness of at least 3 kiloponds (kp). In another embodiment, the tablet further includes a sweetening agent and a color agent.

In other aspects, the invention features a method of administering an active agent to an individual, the method includes making a gel according to a method disclosed herein, the tablet (e.g., effervescent tablet) further including a medicament, and administering the gel to an individual.

In another aspect, the invention features a gelled composition that includes a medicament, at least one of a conjugate base of an acid and an ester of an acid, binder, and lubricant, the medicament being uniformly dispersed throughout the gelled composition. In one embodiment, the medicament is acetaminophen.

In one embodiment, the method of making a gelled composition includes combining a particulate that includes at least 1000 mg gelatin and medicament, and water in a vessel to form an aqueous composition, heating the aqueous composition (e.g., in a microwave oven), the particulate at least partially dissolving during the heating, and chilling the aqueous composition for a period sufficient for the aqueous composition to form a gel.

In other aspects, the invention features a packaged dosage form that includes a sealed package, and from about 1 gram to about 6 grams of a free-flowing particulate disposed in the sealed package, the sealed package comprising at least 1000 mg gelatin and a medicament.

The method of making a gelled composition is simple to perform and does not require the transfer of boiling liquid from one vessel to another. The method also eliminates the need to boil water on a stove when making a gelled composition, although water heated on a stove can be used in the method. The method also eliminates the need for stirring when making gelatin, although the liquid can be stirred.

The single serving and single dose formulations provide gelatin in a form that enables a consumer to easily prepare a dessert or a tasty vehicle for delivering an active agent such as a medicament or a vitamin.

Other features and advantages will be apparent from the following description of the preferred embodiments and from the claims.

Glossary

In reference to the invention, these terms have the meanings set forth below:

The term "effervescent" means the ability to rapidly give off gas bubbles when contacted with water.

DETAILED DESCRIPTION

The method of making a gelled composition includes heating an aqueous composition that includes water and an effervescent tablet, allowing the tablet to dissolve, and then chilling the heated composition to a temperature and for a time sufficient to cause the composition to thicken and for the gel to set. The set gel has a consistency similar to the gelatin food products (e.g., desserts and snacks) available under the JELL-O trade designations from Kraft Foods, Inc. (Northfield, Ill.). When the gel is set, it does not flow. One method of determining gel flow includes inverting an open mouth container in which the gel has been formed 180° and observing whether or not the gel flows out of the open mouth of the container. A gel that does not flow out of the container under such conditions is deemed a set gel. The set gel holds its shape when removed from the container in which it was formed, has a smooth texture in the mouth, and preferably is not rubbery.

The gelled composition is suitable for use as a variety of edible products including, e.g., food products (e.g., desserts and snacks), as a vehicle for delivering an active agent, (e.g., a dosage form), and combinations thereof. The gelled composition can be formed as a single serving food product, a single dose of medicament, and combinations thereof.

The step of heating the aqueous composition preferably includes placing the composition in a microwave oven and heating the composition using microwave radiation (e.g., on the full power setting). Other useful methods of heating can include any suitable heat source including, e.g., a burner on a stove. The tablet dissolves in the heated water. Preferably the tablet is present in the aqueous composition during the heating process and at least partially or completely dissolves during the heating. Although stirring may be required, in the case of effervescent tablets the effervescent action of the dissolving tablet preferably is sufficiently strong to distribute the ingredients of the tablet uniformly throughout the heated liquid so that no stirring is required. Although the aqueous composition has been described as including the tablet during the heating process, alternatively the tablet can be added to the water either prior to, during or after the heating.

The process of chilling the heated composition preferably includes chilling the heated composition to a temperature below 10° C., below 8° C., at about 4° C., or even from about 0° C. to about 8° C. The composition gradually thickens and preferably forms a gel that maintains its shape when removed from the container in which it was made after cooling in an environment of about 4° C. for less than three hours or even no greater than two hours. One useful method of chilling the aqueous composition includes placing the aqueous composition in a refrigerator for a period sufficient for the composition to form a set gel. Other methods of chilling the aqueous composition include, e.g., placing a container of the aqueous composition in a cold water bath, an ice bath, or an ice water bath.

The method optionally includes adding cold water to the heated composition prior to further chilling the composition. Useful sources of cold water include, e.g., cold tap water, cold ice water, refrigerated water, and ice. The cold water preferably has a temperature of from about 0° C. to about 25° C., no greater than about 20° C., no greater than about 15° C., no greater than about 5° C. or even no greater than 0° C. Alternatively, room temperature water can be used.

The container in which the gelatin composition is prepared can be any suitable container including, e.g., a cup (e.g., a six ounce cup, a four ounce cup, and a two ounce cup), a bowl, and a dose dispenser (e.g., a one ounce cup), made from any useful material including, e.g., plastic, metal (e.g., aluminum), glass, and ceramic. The gelatin composition can be prepared in the same container in which it is chilled and from which it is eventually consumed. Particularly useful containers are dimensioned to provide a single food serving or a single dosage form.

The gelled composition optionally includes an active agent and can be used as a vehicle for administering the active agent to a mammal (e.g., a human, a pet (e.g., dog, cat, and rabbit), a farm animal, and a zoo animal). The active agent can be incorporated into the gelled composition using a variety of methods including, e.g., formulating the tablet to include the active agent, combining the active agent and the tablet prior to combining the same with water, combining the active agent and water prior to combining the tablet and the water, adding the active agent to the aqueous mixture of the tablet and water at any point during the method of making the gelatin including, e.g., prior to, during, or after heating the aqueous composition, prior to or during the chilling of the aqueous composition, and prior to, during, or after adding the optional cold water to the aqueous composition, and combinations thereof. The active agent preferably is present in the aqueous composition before the gel solidifies and preferably is uniformly distributed throughout the gelled composition.

A particularly useful method of making a single serving gelled food product includes placing the effervescent tablet in a cup, adding from about 1 ounce to about 3 ounces (or even about 2 ounces) of water (e.g., tap water) to the cup, heating the combination in a microwave during which time the tablet at least partially dissolves, adding from about 1 ounce to about 3 ounces (or even about 2 ounces) of cold water to the heated composition, and placing the heated composition in a cold environment (e.g., a refrigerator) for a period sufficient to form a set gel.

A particularly useful method of making a single dose of an orally ingestible dosage form includes placing a tablet that includes an active agent in a cup, adding from about 0.5 ounces to about 3 ounces of water (e.g., tap water) to the cup, heating the combination in a microwave during which time the tablet at least partially dissolves, adding from about 0.5 ounces to about 3 ounces of cold water to the heated composition, and placing the heated composition in a cold environment (e.g., a refrigerator) for a period sufficient to form a set gel.

The effervescent tablet includes gelatin, an effervescent couple, binder, and lubricant. The gelatin is a food-grade (i.e., edible) gelatin and can be acid or alkaline processed. Useful gelatins exhibit a bloom of from about 100 to about 350 AOAC (Association of Agricultural Chemists), from about 125 to about 300, or even from about 225 to about 275. The gelatin can be derived from a variety of sources including, e.g., bone, cartilage, and hide, from a variety of animals including, e.g., cows and pigs. The gelatin preferably is in the form of powder, granules, or a combination thereof. Particularly useful gelatin has a particle size of 40 mesh. One example of a useful commercially available gelatin is available under the trade designation GELATINE 250 Bloom 40 mesh from PB Leiner (Plainview, N.Y.).

The amount of gelatin present in the effervescent tablet and the amount of water with which the effervescent tablet is combined are preferably selected such that the gelatin composition formed therefrom exhibits the desired gel strength (i.e., it does not flow), and is of the desired serving size (e.g., a single size serving of food product (e.g., a single serving of an edible snack or dessert), a single dose of an active agent (e.g., an herb, a vitamin, a pharmaceutical, an over the counter medicament), a multiple serving food product, a multi-dose dosage form, and combinations thereof. Preferably the ratio of the amount gelatin (mg) to the total amount of water (ml) added to form the gelled composition is at least about 5:1, at least about 6:1, at least about 7:1, no greater than about 20:1, no greater than 18:1, no greater than about 17:1 or even no greater than about 10:1. The gelatin preferably is present in the effervescent tablet in an amount of at least 5% by weight, at least 25% by weight, at least 30% by weight, at least 40% by weight, at least 45% by weight, at least 50% by weight, no greater than about 80% by weight, no greater than about 75% by weight, no greater than about 65% by weight, from about 25% by weight to about 50% by weight, from about 25% by weight to about 45% by weight, or even from about 30% by weight to about 40% by weight. The effervescent tablet preferably includes at least 200 mg, at least 400 mg, at least 800 mg, at least 1000 mg, or even at least 1500 mg, and no greater than 5000 mg, no greater than 4000 mg, no greater than 3000 mg gelatin, no greater than 2500 mg gelatin, or even no greater than 2000 mg gelatin.

The effervescent couple of the effervescent tablet includes a base and an acid. The effervescent couple is activated when contacted with water, e.g., when the tablet is placed in water, to rapidly release gas bubbles. The water liberates the acid and base and enables the acid and base to react with each other to produce carbon dioxide gas. The effervescent couple is preferably present in the effervescent tablet in an amount of at least 10% by weight, at least 15% by weight, from about 15% by weight to about 35% by weight, from about 10% by weight to about 30% by weight, or even from about 20% by weight to about 30% by weight. The effervescent couple is preferably present in the effervescent tablet in an amount of at least 750 mg, at least 800 mg, no greater than 1800 mg, no greater than 1500 mg, or even no greater than 1000 mg.

The base of the effervescent couple preferably is capable of generating a gas such as carbon dioxide. Examples of suitable bases include carbonate bases, e.g., sodium bicarbonate, sodium carbonate, sodium sesquicarbonate, potassium carbonate, potassium bicarbonate, calcium carbonate, magnesium carbonate, and mixtures thereof. The effervescent tablet preferably includes from 2% by weight to about 25% by weight, from about 3% by weight to about 20% by weight, from at least 1% by weight to about 15% by weight, from about 5% by weight to about 15% by weight, or even from about 5% by weight to about 10% by weight base. The base is preferably present in the effervescent tablet in an amount of at least 50 mg, at least 100 mg, at least 200 mg, no greater than 800 mg, no greater than 700 mg, no greater than 600 mg, or even no greater than 500 mg.

A variety of acids are suitable for use in the effervescent couple including, e.g., citric acid, ascorbic acid, aspartic acid, malic acid, adipic acid, tartaric acid, fumaric acid, succinic acid, sodium acid pyrophosphate, lactic acid, hexamic acid, amino acids, and acid salts and acid anhydrides thereof, and mixtures thereof. Examples of useful acid anhydrides include citraconic anhydride, glucono-D-lactone, and succinic anhydride. Examples of useful acid salts include potassium bitartrate, acid citrate salts, sodium dihydrogen phosphate, disodium dihydrogen phosphate, sodium acid sulfite, and combinations thereof. The effervescent tablet preferably includes from 1% by weight to about 25% by weight, from about 5% by weight to about 20% by weight, from about 10% by weight to about 20% by weight, or even from about 10% by weight to 15% by weight acid. The acid is preferably present in the effervescent tablet in an amount of at least 50 mg, at least 250 mg, at least 400 mg, at least 500 mg, no greater than 2500 mg, no greater than 2000 mg, no greater than 1500 mg, no greater than 1000 mg, no greater than 800 mg, no greater than 700 mg, or even no greater than 600 mg.

The binder of the effervescent tablet can be any suitable binder including, e.g., starches, natural gums, cellulose gums, microcrystalline cellulose, methylcellulose, cellulose ethers, sodium carboxymethylcellulose, ethylcellulose, gelatin, dextrose, lactose, sucrose, sorbitol, mannitol, polyethylene glycol, polyvinylpyrrolidone, pectins, alginates, polyacrylamides, polyvinyloxoazolidone, polyvinylalcohols and mixtures thereof. Preferably the binder is water soluble.

Binder is preferably present in the effervescent composition in an amount sufficient to assist in holding the components of the composition together in the form of a tablet, preferably in an amount from about 5% by weight to about 40% by weight, from 10% by weight to about 60% by weight, from about 15% by weight to about 50% by weight, or even from about 20% by weight to about 40% by weight, or even 25% by weight to 35% by weight. The effervescent tablet preferably includes at least 500 mg, at least 1000 mg, at least 1250 mg, at least 1500 mg, no greater than 2500 mg, no greater than 2000 mg, no greater than 1800 mg, or even no greater than 1750 mg binder.

Various lubricants are suitable for use in the effervescent tablet including water dispersible lubricants, water soluble lubricants, water insoluble lubricants, and combinations thereof. Preferred lubricants are water soluble. Some lubricants also provide a binder function and vice versa (i.e., some binders provide a lubricant function). Examples of useful water soluble lubricants include sodium benzoate, polyethylene glycol, L-leucine, adipic acid, and combinations thereof. The composition can also include water insoluble lubricants including, e.g., stearates (e.g., magnesium stearate, calcium stearate and zinc stearate), oils (e.g., mineral oil, hydrogenated and partially hydrogenated vegetable oils, cotton seed oil, and wheat germ oil) and combinations thereof. Other water insoluble lubricants include, e.g., animal fats, polyoxyethylene monostearate, talc, and combinations thereof.

The effervescent tablet preferably includes a sufficient amount of lubricant to enable the composition to be formed into tablets and released from a high speed tableting press in the form of a tablet. The effervescent tablet preferably includes at least 0.05% by weight, at least 0.1% by weight, at least 0.5% by weight, no greater than 10% by weight, no greater than 6% by weight, or even no greater than 2% by weight, or even from about 0.5% by weight to about 1% by weight lubricant. The lubricant is preferably present in the effervescent tablet in an amount of at least 5 mg, at least 10 mg, at least 20 mg, or even at least 25 mg, and no greater than 200 mg, no greater than 150 mg, no greater than 35 mg, or even no greater than 30 mg.

The effervescent tablet optionally includes a desiccant. A variety of desiccants can be used in the effervescent tablet including, e.g., potassium carbonate, sodium carbonate, magnesium oxide, and combinations thereof.

Active agents that are optionally present in the gelled composition, the effervescent tablet or a combination thereof, include, e.g., medicaments, vitamins, minerals, amino acids, other dietary supplements, herbs, and combinations thereof. The gelled composition is particularly useful for delivering medicaments that are bitter tasting or otherwise unpalatable, as the gelled composition can provide a dosage form for the medicaments that is more palatable or even tasty relative to the medicament itself. Examples of medicaments include prescription drugs, over the counter drugs (e.g., aspirin (acetylsalicylic acid), acetaminophen, ibuprofen, dextromethorphan, and chlorpheniramine), and combinations thereof.

Examples of useful vitamins include, e.g., ascorbic acid (vitamin C), aspartic acid, thiamin, riboflavin, nicotinic acid, pantothenic acid, pyridoxine, biotin, folic acid, niacin, vitamin B12, lipoic acid, vitamin A, vitamin D, vitamin E and vitamin K and coenzymes thereof, choline, carnitine, and alpha, beta, and gamma carotenes. Examples of coenzymes include thiamine pyrophosphates, flavin mononucleotide, flavin adenine dinucleotide, nicotinamide adenine dinucleotide, nicotinamide adenine dinucleotide phosphate coenzyme A pyridoxal phosphate, biocytin, tetrahydrofolic acid, coenzyme B12, lipoyllysine, 11-cis-retinal, and 1,25-dihydroxycholecalciferol, and mixtures thereof.

Examples of useful minerals include iron, zinc, calcium, sodium, potassium, manganese, selenium, copper, iodine, magnesium, phosphorus, and chromium and combinations thereof.

Suitable amino acids include, e.g., L-tyrosine, isoleucine, ornithine, glutamine, phenylalanine, leucine, lysine, methionine, threonine, taurine, tryptophan, valine, alanine, glycine, arginine, histidine, cysteine, asparagine, proline and serine, and combinations thereof.

Other dietary supplements include, e.g., bee pollen, bran, wheat germ, kelp, cod liver oil, ginseng, fish oils, proteins, and combinations thereof.

Useful herbs include, e.g., ginger, sage, thyme, red clover, black cohosh, and combinations thereof, and extracts thereof.

The effervescent tablet optionally includes other ingredients including, e.g., flavor agents, coloring agents (e.g., dyes and pigments), sweetening agents, other gelling agents (e.g., pectin, cellulose, carboxymethyl cellulose, carrageenan, starch, and sodium alginate), fillers, surfactants (e.g., polysorbate 80 and sodium lauryl sulfate), and flow agents and combinations thereof.

Useful flavor agents include natural and artificial flavor agents including, e.g., volatile oils, synthetic flavor oils, flavoring aromatics, oils, liquids, oleoresins and extracts derived from plants, leaves, flowers, fruits, stems and combinations thereof. Useful flavor agents include, e.g., citric oils, e.g., lemon, orange, grape, lime and grapefruit, fruit essences including, e.g., apple, pear, peach, grape, strawberry, raspberry, cherry, plum, pineapple, apricot, and other fruit flavors, ice tea flavoring, and combinations thereof. Other useful flavor agents include, e.g., aldehydes and esters (e.g., benzaldehyde (cherry, almond)), citral, i.e., alpha-citral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanal (green fruit), 2-dodedenal (citrus, mandarin), and mixtures thereof. Preferably the effervescent tablet includes from about 0.1% by weight to about 10% by weight, or even from about 0.5% by weight to about 5% by weight flavor agent, at least about 30 mg, at least about 100 mg, at least about 200 mg, no greater than about 500 mg, no greater than about 400 mg flavor agent, or even from about 100 mg to about 150 mg.

Useful color agents include, e.g., food, drug and cosmetic (FD&C) colors including, e.g., dyes (e.g., FD&C Red No. 3, FD&C Red No. 40, FD&C Blue No. 1, FD&C Yellow No. 5, FD&C Yellow No. 5, and FD&C Green No. 3), lakes, and certain natural and derived colorants. Useful lakes include dyes absorbed on aluminum hydroxide and other suitable carriers.

Useful sweetening agents include stevia, sugars such as sucrose, glucose, invert sugar, fructose, ribose, tagalose, sucralose, malitol, erythritol, xylitol, and mixtures thereof, saccharin and its various salts (e.g., sodium and calcium salt of saccharin), cyclamic acid and its various salts, dipeptide sweeteners (e.g., aspartame), acesulfame potassium, dihydrochalcone, glycyrrhizin, and sugar alcohols including, e.g., sorbitol, sorbitol syrup, mannitol and xylitol, and combinations thereof. Preferably the effervescent tablet includes from about 0.01% by weight to about 5% by weight, or even from about 0.1% by weight to about 5% by weight sweetening agent, at least about 5 mg, at least about 10 mg, at least about 20 mg, no greater than about 100 mg, no greater than about 50 mg, or even from about 25 mg to about 40 mg sweetening agent.

The components of the effervescent tablet are preferably dried and sieved as necessary prior to formulating.

The effervescent composition used to form the effervescent tablets is well suited to the mass production of effervescent tablets that are free from picking, die wall etching, capping and lamination. Any suitable tablet mass production equipment and processes can be used. Examples of useful tableting processes for effervescent compositions are described in Pharmaceutical Dosage Forms, Vol. 1 (Herbert A. Lieberman et al. eds, $2^{nd}$ ed. 1989) and incorporated herein. The tablets can then be manufactured in an automated process in which multiple dies of a tablet press are filled sequentially or simultaneously with the effervescent composition, two punches compress the effervescent composition to form the tablet(s), and then the tablet(s) is ejected from the die. Useful effervescent tablets have a mass of from about 1 g to about 6 g, from about 2 g to about 5 g, or even from about 3 g to about 4.5 g, and a hardness of at least 1 kiloponds (kp), at least 2.5 kp, at least 3 kp, at least 4 kp, from about 2 kp to about 10 kp, or even from about 5 kp to about 8 kp, as measured on a standard hardness tester fitted with a strain gauge. The tablet can have any suitable diameter including, e.g., at least about 10 mm (millimeters), from about 15 mm to about 30 millimeters, or even from about 17 mm to about 25 mm.

The tablet is then placed in packaging material, which is then sealed to form an air tight sealed package. The packaged tablet can be further processed by conveying it to other processing stations including, e.g., additional packaging stations for further packaging, e.g., boxing and bagging.

The tablet manufacturing and initial packing operations are preferably performed in a controlled environment in which the temperature and humidity are controlled. Preferably the controlled environment has less than 18 grains, less than 16 grains, or even less than 15 grains of moisture.

Although the method has been described in conjunction with the use of an effervescent tablet, the method can alternatively be practiced using an effervescent particulate (e.g., a powder or granulation), a non-effervescent particulate, or a tablet that is not effervescent. The particulate is preferably a free flowing particulate, or even a dry, free flowing particulate. Particulate effervescent formulations include the same ingredients in the same or similar amounts as set forth above with respect to the effervescent tablet formulation with the exception that binder and lubricant are not required and can be omitted from the effervescent formulation.

A non-effervescent tablet can be prepared using the same components as set forth above with the exception that either the acid or the base of the effervescent couple, or both the acid and the base can be omitted from the composition. Useful non-effervescent tablets have a mass of from about 1 g to about 6 g, from about 2 g to about 5 g, or even from about 3 g to about 4.5 g.

A non-effervescent dry, free flowing particulate can be prepared using the same components as set forth above with the exception that at least one of the components of the effervescent couple, the lubricant and the binder can be omitted from the composition.

The tablets and particulate are preferably stored in moisture-proof package including, e.g., metal foil pouches, sleeves, sticks, sachets, blister packs, and desiccant capped tubes. Useful packaging materials further include metal foil, plastic films, multilayer constructions (e.g., constructions that include layers of metal foil, polymer film, paper, and combinations thereof) and blister packaging. The packaging can be in the form of a package that includes a single unit (e.g., dose or serving) or multiple units. The packaging can be sealed using any suitable sealing technique including, e.g., heat, pressure, adhesive, sonic welding, and combinations thereof.

Useful single unit packages that include particulate include from about 1 g to about 6 g, from about 2.5 g to about 5 g, or even from about 3 g to about 4.5 g particulate.

The method can optionally include opening the sealed packaging and allowing the contents (e.g., the tablet or the particulate) of the sealed package to pass from the package into the vessel (e.g., the empty vessel or water in the vessel), preferably without the contents of the package contacting the user.

The invention will now be described by way of the following examples. All parts, ratios, percents and amounts stated in the Examples are by weight unless otherwise specified.

EXAMPLES

Test Procedures

Test procedures used in the examples include the following. All ratios and percentages are by weight unless otherwise indicated.

BASE 1

A base was prepared by combining 540 mg fine granular citric acid, 500 mg Sorbitol G3, and 30 mg mineral oil with mixing using a KITCHEN AID mixer.

BASE 2

Base 2 was prepared by combining 150 mg potassium carbonate, 75 mg sodium carbonate, 114 mg aspartame, 50 mg flavor agent, 40 mg potassium bicarbonate, 35 mg sodium bicarbonate, 10 mg color agent, 7 mg ascorbic acid, 6 mg acesulfame K, 5.5 mg sodium benzoate and 1 mg sucralose with mixing using a KITCHEN AID mixer.

Example 1

An effervescent composition was prepared by combining, with manual agitation, 1070 mg Base 1, 493.5 mg Base 2, and 4000 mg 250 bloom 40 mesh gelatin until a uniform mixture was obtained. An attempt was then made to tablet the effervescent composition using one inch flat faced steel tools. The tablets formed had an average hardness of 1 kp. It was observed that the gelatin was not very compressible and seemed elastic.

The tablet of Example 1 was placed in a cup containing three ounces of 70° C. water whereupon it began to effervesce. A gel layer formed around the tablet and the tablet floated in the water. The mixture needed to be stirred. The tablet completely dissolved in less than two minutes. Three ounces of cold water were then added to the heated composition. The resulting composition was then placed in a refrigerator at about 4° C. overnight and was in the form of a rigid gel the next morning. The taste was acceptable. The gel did not release from the cup when the cup was inverted.

Example 2

An effervescent composition was prepared by combining, with manual agitation, 1070 mg Base 1, 493.5 mg Base 2, and 3000 mg 250 bloom 40 mesh gelatin until a uniform mixture was obtained. The effervescent composition was then made into tablets using one inch flat faced steel tools. The tablets formed had a hardness of from 2.6 kp to 3.5 kp.

A tablet of Example 2 was placed in a cup containing three ounces of 83° C. water. The tablet floated to the surface of the water and quickly began effervescing and then the effervescence quickly slowed down. The tablet completely dissolved in less than one minute with vigorous stirring. Three ounces of cold water was then added to the heated composition. The resulting composition was then placed in a refrigerator at about 4° C. overnight and, the next morning, was in the form of a rigid gel that held its shape. The gel did not release form the cup when the cup was inverted, and exhibited good texture and consistency and a stable structure.

Example 3

An effervescent tablet was prepared by combining, with manual agitation, 1070 mg Base 1, 493.5 mg Base 2, and 2500 mg 250 bloom 40 mesh gelatin until a uniform mixture was obtained. The effervescent composition was then made into a tablet using one inch flat faced steel tools. The tablets had an average hardness of about 5.9 kp.

A tablet of Example 3 was placed in a cup containing three ounces of 80° C. water and completely dissolved in less than one minute. Three ounces of cold water were then added to the heated composition. The resulting composition was then placed in a refrigerator at 4° C. overnight and, in the morning, was in the form of a firm gel. The gel did not release from the cup when the cup was inverted, and exhibited good texture and a stable structure.

Example 4

An effervescent tablet was prepared by combining, with manual agitation, 1070 mg Base 1, 493.5 mg Base 2, and 2000 mg 250 bloom 40 mesh gelatin, until a uniform mixture was obtained. The effervescent composition was then made into a tablet using one inch flat faced steel tools. The tablets formed had an average hardness of 6.2 kp.

The tablet of Example 4 was then placed in a cup containing three ounces of 80° C. water and completely disintegrated in less than one minute. Almost all of the particles of the tablet also dissolved in less than one minute. The composition was stirred to facilitate complete dissolution. Three ounces of cold tap water was then added to the heated composition. The resulting composition was then placed in a refrigerator at about 4° C. overnight and was in the form of a gel the next morning. The gel jiggled and fell out of the cup when the cup was inverted.

Example 5

An effervescent composition was prepared by combining, with manual agitation, 800 mg granular citric acid, 1500 mg sorbitol instant, 100 mg potassium carbonate, 120 mg flavor, 25 mg Acesulfame potassium, 8 mg sucralose, 1666.67 gelatin 250 bloom 40 mesh gelatin, 180.51 mg acetaminophen, 6 mg color agent, and 25 mg wheat germ oil until a uniform mixture was obtained. The effervescent composition was then made into a tablet using one inch flat faced steel tools. The tablets formed had an average hardness of 5.1 kp.

A tablet of Example 5 was placed in a cup containing four ounces of tap water, which was then placed in a microwave and heated for 55 seconds. The tablet completely dissolved in less than one minute. The resulting composition was then placed in a refrigerator at 4° C. overnight and, in the morning, was in the form of a set gel.

Example 6

An effervescent composition was prepared according to Example 5 with the exception that the composition included no acetaminophen and further included 550 mg sodium carbonate and 114.58 mg ibuprophen. The tablets formed from the effervescent composition of Example 6 had a hardness of 4.7 kp.

A tablet of Example 6 was placed in a cup containing four ounces of tap water, which was then placed in a microwave and heated for 55 seconds. The tablet completely dissolved in less than one minute. The resulting composition was then placed in a refrigerator at 4° C. and formed a set gel after two hours. The gel tasted ok, but was a little bitter.

Example 7

An effervescent composition was prepared according to Example 5 with the exception that the amount of granular citric acid was 600 mg, the amount of sorbitol instant was 1700 mg, the amount of flavor was 160 mg, the amount of sucralose was 12 mg, and the amount of acesulfame potassium was 35 mg, and the composition further included 350 mg sodium bicarbonate. The tablets formed from the effervescent composition of Example 7 had a hardness of 6.2 kp.

A tablet of Example 7 was placed in a cup containing four ounces of tap water, which was then placed in a microwave and heated for 55 seconds. The tablet was not quite completely dissolved when the cup was removed from the microwave.

A second tablet of Example 7 was placed in a cup containing four ounces of tap water, which was then placed in a microwave and heated for 60 seconds. The tablet was not quite completely dissolved when the cup was removed from the microwave; however less of the tablet remained relative to the first tablet.

Both tablets then completely dissolved within from 20 seconds to 30 seconds after being removed from the microwave and with some stirring.

The resulting compositions were then placed in a refrigerator at 4° C. overnight and, in the morning, were in the form of set gels.

Example 8

An effervescent composition was prepared according to Example 7 with the exception that the composition included no acetaminophen, the amount of sodium benzoate was 50 mg, and the amount of sucralose was 18 mg, and the composition further included 171.88 mg ibuprofen. The tablets formed from the effervescent composition of Example 8 had a hardness of 5.8 kp.

A tablet of Example 8 was placed in a cup containing four ounces of tap water, which was then placed in a microwave and heated for 70 seconds. The tablet was almost completely dissolved when the cup was removed from the microwave.

A second tablet of Example 8 was placed in a cup containing four ounces of tap water, which was then placed in a microwave and heated for 60 seconds. The tablet was not quite completely dissolved when the cup was removed from the microwave. The resulting composition were then placed in a refrigerator at 4° C. overnight and, in the morning, were in the form of set gels. The gel had a bitter taste similar to that of an orange rind.

All patents and publications referred to herein are incorporated herein in their entirety.

Other embodiments are within the claims. For example, in one embodiment, the aqueous composition formed from the combination of water and an effervescent tablet is heated until a foam layer is present on the surface of the composition. The foam layer can rise to a height of at least 1 cm, at least 2.5 cm, at least 3 cm, or even at least 5 cm as measured from the surface of the liquid.

Although the effervescent tablet has been described above in conjunction with the formation of single serving orally ingestible products, the effervescent tablet can be formulated to enable a user to form a multi-serving orally ingestible product, e.g., bowl of gelatin dessert. In addition, multiple effervescent tablets can be used in the method to form the gelled composition.

What is claimed is:

1. An effervescent composition comprising:
   from about 10% by weight to about 30% by weight of an effervescent couple comprising an acid and a base;
   from at least 5% by weight to about 20% by weight of the acid;
   from at least 1% by weight to about 15% by weight of the base; and
   at least 200 mg of a gelatin that forms a gel, the gelatin comprising gelatin derived from a cow, gelatin derived from a pig, or a mixture thereof,
   the effervescent composition forming a gel when the effervescent composition is dissolved in heated water to form an aqueous composition and the aqueous composition is subsequently chilled.

2. The effervescent composition of claim 1 comprising from about 10% by weight to about 20% by weight of the acid and from at least 5% by weight to about 15% by weight of the base.

3. An effervescent tablet comprising the effervescent composition of claim 1, comprising at least 30% by weight of the gelatin, and further comprising
   from about 5% by weight to about 40% by weight binder; and
   from about 0.5% by weight to about 1% by weight lubricant.

4. The effervescent tablet of claim 3 comprising at least about 1000 mg of the gelatin.

5. The effervescent tablet of claim 3 comprising at least about 1500 mg of the gelatin.

6. The effervescent tablet of claim 3 having a hardness of at least 3 Kp.

7. The effervescent tablet of claim 3 further comprising a sweetening agent and a color agent.

8. The composition of claim 1, wherein the composition is a uniform mixture.

9. The composition of claim 1, wherein the composition is the form of a free flowing particulate or a tablet.

10. The composition of claim 1, wherein the gelatin comprises gelatin derived from a pig.

11. A packaged dosage form comprising:
    a sealed package; and
    from about 1 gram to about 6 grams of a free-flowing particulate disposed in the sealed package, the free-flowing particulate comprising the effervescent composition of claim 1, at least 1000 mg of a gelatin that forms a gel and a medicament.

12. A method of making a gelled composition, the method comprising:
    combining the effervescent composition of claim 1 and water in a vessel to form an aqueous composition;
    heating the aqueous composition in a microwave oven, the effervescent composition at least partially dissolving during the heating; and
    chilling the aqueous composition for a period sufficient for the aqueous composition to form a gel.

13. The method of claim 12, wherein the chilling occurs in an environment having a temperature of no greater than 8° C.

14. The method of claim 12, wherein the composition forms a set gel in less than two hours when chilled at a temperature of from about 0° C. to about 8° C.

15. The method of claim 12 further comprising adding cold water having a temperature of from about 0° C. to about 25° C. to the heated aqueous composition.

16. The method of claim 12, wherein the gel is a set gel.

17. The method of claim 12, wherein combining the water and the effervescent tablet comprises placing from about 1 ounce to about 3 ounces of water in the vessel.

18. The method of claim 15, wherein adding cold water comprises adding from about 1 ounce to about 3 ounces of cold water.

19. The method of claim 12, wherein the effervescent composition comprises at least about 400 mg of the gelatin.

20. The method of claim 19, wherein combining the water and the effervescent composition comprises placing about 0.5 ounces of water in the vessel.

21. The method of claim 20 further comprising adding about 0.5 ounces of cold water having a temperature of from about 0° C. to about 25° C. to the heated aqueous composition.

22. The method of claim 12, wherein the effervescent composition comprises at least about 1000 mg of the gelatin.

23. The method of claim 12, wherein the effervescent composition comprises at least about 1500 mg of the gelatin.

24. The method of claim 12, wherein the effervescent composition comprises from about 1000 mg to about 5000 mg of the gelatin.

25. The method of claim 12, wherein the composition forms a set gel in no greater than two hours.

26. A method of making a gelled composition, the method comprising:
    heating an aqueous composition comprising the effervescent composition of claim 1 and water, the effervescent composition at least partially dissolving during the heating; and
    chilling the composition to form a set gel.

27. The method of claim 26, wherein the heating comprises heating the aqueous composition in a microwave oven.

28. The method of claim 26, wherein the effervescent composition comprises at least 1000 mg of the gelatin.

29. The method of claim 26 further comprising adding cold water having a temperature of no greater than 25° C. to the heated aqueous composition.

30. The method of claim 29, wherein the adding cold water comprises adding from about 1 ounce to about 3 ounces of cold water, the cold water having a temperature of from about 0° C. to about 25° C.

31. The method of claim 29, further comprising:
    placing the effervescent composition in a vessel; and
    placing from about 1 ounces to about 3 ounces of tap water in the vessel,
    the adding cold water comprising adding from about 1 ounce to about 3 ounces of the cold water,
    the step of chilling the aqueous composition comprising placing the heated aqueous composition in a refrigerator.

32. A method of administering an active agent to an individual, the method comprising:
    making a gel according to the method of claim 12, the effervescent tablet further comprising a medicament; and
    administering the gel to an individual.

33. A method of making a gelled composition, the method comprising:
    combining the effervescent composition of claim 3 and water in a vessel to form an aqueous composition;

heating the aqueous composition in a microwave oven, the tablet at least partially dissolving during the heating; and chilling the aqueous composition for a period sufficient for the aqueous composition to form a gel.

34. The method of claim 33, wherein the effervescent tablet further comprises a medicament.

35. A method of making a gelled composition, the method comprising:

combining
- a particulate comprising the effervescent composition of claim 1 comprising at least 1000 mg of the gelatin, and medicament, and
- water in a vessel to form an aqueous composition;

heating the aqueous composition in a microwave oven, the particulate at least partially dissolving during the heating; and chilling the aqueous composition for a period sufficient for the aqueous composition to form a gel.

36. A method of making a gelled composition, the method comprising:

combining the effervescent composition of claim 1 and water to form an aqueous composition; and allowing the effervescent composition to at least partially dissolve.

37. The method of claim 36, wherein the combining comprises adding the effervescent composition to heated water.

38. The method of claim 36, wherein the combining comprises adding the effervescent composition to water having a temperature of at least 70° C.

39. The method of claim 36, wherein the combining comprises adding the effervescent composition to water having a temperature of at least 80° C.

40. The method of claim 39 further comprising chilling the aqueous composition.

* * * * *